United States Patent [19]

Jensen-Korte et al.

[11] Patent Number: 4,810,720
[45] Date of Patent: Mar. 7, 1989

[54] PESTICIDAL 1-ARYLPYRAZOLES, COMPOSITIONS AND USE

[75] Inventors: Uta Jensen-Korte, Duesseldorf; Otto Schallner, Monheim; Jörg Stetter, Wuppertal; Heinz-Jürgen Wroblowsky, Langenfeld; Wilhelm Stendel, Wuppertal; Benedikt Becker, Mettmann; Bernhard Homeyer, Leverkusen; Wolfgang Behrenz, Overath-Steinbrueck, all of Fed. Rep. of Germany

[73] Assignee: Bayer Aktiengesellschaft, Leverkusen, Fed. Rep. of Germany

[21] Appl. No.: 947,800

[22] Filed: Dec. 30, 1986

[30] Foreign Application Priority Data

Jan. 8, 1986 [DE] Fed. Rep. of Germany ....... 3600287

[51] Int. Cl.⁴ .............. A01N 43/40; A01N 43/56; C07D 231/18; C07D 401/04
[52] U.S. Cl. ..................... 514/407; 514/341; 546/279; 548/375; 548/377
[58] Field of Search .............. 548/375, 377; 546/279; 514/407, 341

[56] References Cited

U.S. PATENT DOCUMENTS

| | | | |
|---|---|---|---|
| 3,609,185 | 9/1971 | Yeomans et al. | 562/509 |
| 3,932,508 | 1/1976 | Throckmorton | 564/268 |
| 3,937,738 | 2/1976 | Throckmorton | 568/42 |
| 4,127,575 | 11/1978 | McGregor | 546/345 |

FOREIGN PATENT DOCUMENTS

| | | |
|---|---|---|
| 2138728 | 2/1972 | Fed. Rep. of Germany . |
| 2558399 | 7/1976 | Fed. Rep. of Germany . |
| 3012597 | 10/1980 | Fed. Rep. of Germany . |

OTHER PUBLICATIONS

J. Org. Chem., 49, 3494–3498 (1984).
Chem. Ber. 106, 1418–1422 (1973).
Zh. Org. Khim. 8, 1990–1991 (1972).
J. Org. Chem., 36, 2972–2974 (1971).
J. Heterocyclic Chem. 7, 345–349 (1970).
J. Org. Chem., 46, 153–157 (1981).
Il Farmaco-Ed. Sc.–vol. 38-fasc. 4 (1982).
Chemical Abstracts, vol. 85, No. 1, 5. July 1976, p. 454.

*Primary Examiner*—Robert W. Ramsuer
*Attorney, Agent, or Firm*—Sprung Horn Kramer & Woods

[57] ABSTRACT

Insecticidally active 1-aryl-pyrazoles of the formula

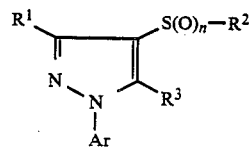

in which
R¹ represents hydrogen, alkyl or haloalkyl,
R² represents alkyl, alkenyl, alkinyl, cycloalkyl, haloalkyl, haloalkenyl, alkoxyalkyl, alkylthioalkyl, alkylsulphinylalkyl, alkylsulphonylalkyl, optionally substituted aralkyl or optionally substituted aryl,
R³ represents alkyl, haloalkyl, cycloalkyl or optionally substituted aryl,
Ar represents subsituted phenyl, with the exception of the 4-nitrophenyl radical or the 2,4-dinitrophenyl radical, or represents optionally substituted pyridyl, and
n represents a number 0, 1 or 2.

20 Claims, No Drawings

PESTICIDAL 1-ARYLPYRAZOLES, COMPOSITIONS AND USE

The invention relates to novel 1-arylpyrazoles, a process for their preparation, and their use as pesticides, particularly as insecticides.

It is already known that certain pyrazole derivatives, such as, for example, 1-cyclohexyl-5-[N,N-(dimethyl)-carbamoyloxy]-3-methylthiomethyl-pyrazole, 1-cyclohexyl-5-[N,N-(dimethyl)-carbamoyloxy]-3-methylsulphinylmethylpyrazole or 1-cyclohexyl-5-[N,N-(dimethyl)-carbamoyloxy]-3-methylsulphonylmethyl-pyrazole have an insecticidal action.

However, the strength of action or the duration of action of these compounds is not always completely satisfactory in all areas of application, particularly for certain insects or at low applicational concentrations.

Novel 1-aryl-pyrazoles of the general formula (I)

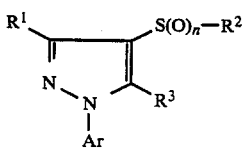 (I)

in which

R¹ represents hydrogen, alkyl or haloalkyl,

R² represents alkyl, alkenyl, alkinyl, cycloalkyl, haloalkyl, haloalkenyl, alkoxyalkyl, alkylthioalkyl, alkylsulphinylalkyl, alkylsulphonylalkyl, optionally substituted aralkyl or optionally substituted aryl, R³ represents alkyl, haloalkyl, cycloalkyl or optionally substituted aryl, Ar represents substituted phenyl, with the exception of the 4-nitrophenyl radical or the 2,4-dinitrophenyl radical, or represents optionally substituted pyridyl and n represents a number 0, 1 or 2, have now been found.

It has furthermore been found that the novel 1-aryl-pyrazoles of the general formula (I),

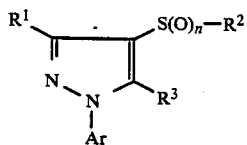 (I)

in which

R¹ represents hydrogen, alkyl or haloalkyl,

R² represents alkyl, alkenyl, alkinyl, cycloalkyl, haloalkyl, haloalkenyl, alkoxyalkyl, alkylthioalkyl, alkylsulphinylalkyl, alkylsulphonylalkyl, optionally substituted aralkyl or optionally substituted aryl, R³ represents alkyl, haloalkyl, cycloalkyl or optionally substituted aryl, Ar represents substituted phenyl, with the exception of the 4-nitrophenyl radical or the 2,4-dinitrophenyl radical, or represents optionally substituted pyridyl and n represents a number 0, 1 or 2, can be obtained by one of the preparation processes described below.

1-Aryl-pyrazoles of the formula (Ia),

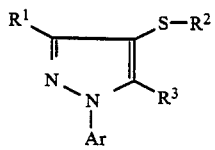 (Ia)

in which

R¹, R², R³ and Ar have the abovementioned meaning, are obtained when (a) arylhydrazines of the formula (II)

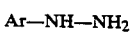 (II)

in which

Ar has the abovementioned meaning, or their acid addition salts, are reacted with 1,3-diketones of the formula (IIIa)

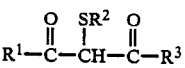 (IIIa)

in which

R¹, R² and R³ have the abovementioned meaning, or, alternatively, are reacted with α,β-unsaturated ketones of the formula (IIIb),

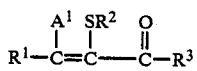 (IIIb)

in which

R¹, R² and R³ have the abovementioned meaning and

A¹ represents a leaving group, such as, for example, alkoxy or dialkylamino, if appropriate in the presence of a diluent and if appropriate in the presence of a catalyst.

1-Arylpyrazoles of the formula (Ib),

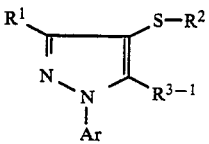 (Ib)

in which

R¹, R² and Ar have the abovementioned meaning and

R³⁻¹ represents optionally substituted aryl, are alternatively obtained when (b) 5-amino-1-aryl-pyrazoles of the formula (IV)

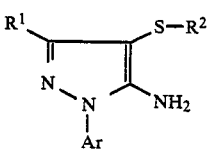 (IV)

are reacted with aromatics of the formula (V),

 (V)

in which

R³⁻¹ has the abovementioned meaning, in the presence of an alkyl nitrite of the formula (VI), $$R^4—O—N=O \qquad (VI)$$

in which

R⁴ represents alkyl and if appropriate in the presence of a diluent.

4-Sulphinyl- and 4-sulphonyl-1-aryl-pyrazoles of the formula (Ic),

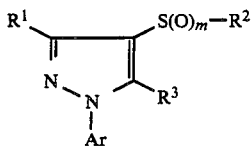

(Ic)

in which

R¹, R², R³ and Ar have the abovementioned meaning and m represents a number 1 or 2, are obtained when (c) the 1-arylpyrazoles of the formula (Ia),

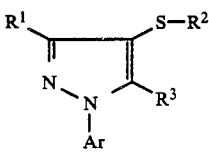

(Ia)

in which

R¹, R², R³ and Ar have the abovementioned meaning, which can be obtained by process (a) or (b), are oxidized in a conventional fashion using oxidants, if appropriate in the presence of a diluent and if appropriate in the presence of a catalyst.

Finally, it has been found that the novel 1-aryl-pyrazoles of the general formula (I) have pesticidal and, in particular, insecticidal properties.

Surprisingly, the 1-aryl-pyrazoles, according to the invention, of the general formula (I) display a substantially better insecticidal activity than the pyrazole derivatives which are known from the state of the art, such as, for example, 1-cyclohexyl-5-[N,N-(dimethyl)-carbamoyloxy]-3-methylthiomethyl-pyrazole or 1-cyclohexyl-5-[N,N-(dimethyl)-carbamoyloxy]-3-methylsulphonylmethylpyrazole, which are similar compounds both chemically and regarding their action.

The 1-aryl-pyrazoles according to the invention are generally defined by the formula (I). Preferred compounds of the formula (I) are those in which R¹ represents hydrogen, or in each case straight-chain or branched alkyl or haloalkyl having 1 to 4 carbon atoms and optionally 1 to 9 identical or different halogen atoms, R² represents in each case straight-chain or branched alkyl, alkenyl, or alkinyl having up to 8 carbon atoms in each case, cycloalkyl having 3 to 7 carbon atoms, in each case straight-chain or branched haloalkyl or haloalkenyl having up to 8 carbon atoms in each case and up to 17 identical or different halogen atoms, in each case straight-chain or branched alkoxyalkyl, alkylthioalkyl, alkylsulphinylalkyl or alkylsulphonylalkyl having 1 to 6 carbon atoms in each of the individual alkyl moieties, or phenylalkyl or phenyl, optionally having 1 to 4 carbon atoms in the straight-chain or branched alkyl moiety, which are in each case optionally mono- or polysubstituted in the phenyl moiety, the substituents being identical or different and suitable substituents in the phenyl moiety being: halogen, cyano, nitro, in each case straight-chain or branched alkyl, alkoxy, alkylthio, alkylsulphinyl, alkylsulphonyl, haloalkyl, haloalkoxy, haloalkylthio, haloalkylsulphinyl or haloalkylsulphonyl having 1 to 4 carbon atoms in each of the individual alkyl moieties and optionally having 1 to 9 identical or different halogen atoms, R³ represents in each case straight-chain or branched alkyl or haloalkyl having 1 to 6 carbon atoms in each case and optionally having 1 to 12 identical or different halogen atoms, cycloalkyl having 3 to 7 carbon atoms or optionally mono- or polysubstituted phenyl, the substituents being identical or different and suitable phenyl substituents being those mentioned for R², Ar represents mono- or polysubstituted phenyl, with the exception of the 4-nitrophenyl or the 2,4-dinitrophenyl radical, the substituents being identical or different, or in each case optionally mono- or polysubstituted 2-pyridyl, 3-pyridyl or 4-pyridyl, the substituents being identical or different and suitable substituents in each case being: cyano, nitro, halogen, in each case straight-chain or branched alkyl, alkoxy or alkoxycarbonyl having 1 to 4 carbon atoms in each case, in addition in each case straight-chain or branched haloalkyl or haloalkoxy having 1 to 4 carbon atoms in each case and 1 to 9 identical or different halogen atoms, or a —S(O)$_p$—R⁵ radical, where R⁵ represents amino and also in each case straight-chain or branched alkyl, alkylamino, dialkylamino or haloalkyl having 1 to 4 carbon atoms in each of the individual alkyl moieties and, in the case of haloalkyl, having 1 to 9 identical or different halogen atoms, p represents a number 0, 1 or 2 and n represents a number 0, 1 or 2.

Particularly preferred 1-arylpyrazoles of the formula (I) are those in which

R¹ represents hydrogen, methyl, ethyl, n- or i-propyl or trifluoromethyl,

R² represents methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, cyclopropyl, cyclobutyl, cyclopentyl, cyclohexyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl, fluorochlorobromomethyl, chloroallyl, fluoroallyl, chlorobutenyl, fluorobutenyl, dichloroallyl, fluorochloroallyl, difluoroallyl, bromoallyl, methoxymethyl, methoxyethyl, methoxypropyl, ethoxymethyl, ethoxyethyl, methylthiomethyl, methylsulphinylmethyl, methylsulphonylethyl, methylthioethyl, methylthiopropyl, methylsulphinylethyl, methylsulphonylmethyl or in each case optionally mono- to trisubstituted phenyl, benzyl or phenylethyl, the substituents being identical or different and suitable phenyl substituents being: fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl or tifluoromethylsulphonyl, $R^3$ represents methyl, ethyl, n- or i-propyl, n-, i-, s- or t-butyl, cyclopropyl, cyclobutyl, cyclopentyl, cyclohexyl, chloromethyl, dichloromethyl, trichloromethyl, bromomethyl, dibromomethyl, fluoromethyl, difluoromethyl, trifluoromethyl, fluorodichloromethyl, difluorochloromethyl or optionally mono- to trisubstituted phenyl, the substituents being identical or different and suitable phenyl substituents being those mentioned for $R^2$, Ar represents mono- to pentasubstituted phenyl, with the exception of the 4-nitrophenyl radical or the 2,4-dinitrophenyl radical, the substituents being identical or different, or in each case optionally mono- to tetrasubstituted 2-pyridyl or 4-pyridyl, the substituents being identical or different and suitable phenyl or pyridyl substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a —$S(O)_p$—$R^5$ radical, where $R^5$ represents amino, methylamino, ethylamino, dimethylamino, diethylamino, fluorodichloromethyl, difluorochloromethyl, tetrafluoroethyl, trifluorochloroethyl, trifluoromethyl, methyl or ethyl, p represents a number 0, 1 or 2 and n represents a number 0, 1 or 2.

Apart from the compounds mentioned in the preparation examples, the following 1-arylpyrazoles of the general formula (I) may be mentioned individually:

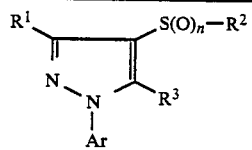

| $R^1$ | $R^2$ | $R^3$ | n | Ar |
|---|---|---|---|---|
| H | CH$_3$ | CH$_3$ | 0 | 2,6-Cl$_2$-4-CF$_3$-C$_6$H$_2$ |
| H | CH$_3$ | CH$_3$ | 1 | 2,6-Cl$_2$-4-CF$_3$-C$_6$H$_2$ |
| H | CH$_3$ | CH$_3$ | 2 | 2,6-Cl$_2$-4-CF$_3$-C$_6$H$_2$ |
| CH$_3$ | CH$_3$ | CH$_3$ | 0 | 2,6-Cl$_2$-4-CF$_3$-C$_6$H$_2$ |
| CH$_3$ | CH$_3$ | CH$_3$ | 1 | 2,6-Cl$_2$-4-CF$_3$-C$_6$H$_2$ |
| CH$_3$ | CH$_3$ | CH$_3$ | 2 | 2,6-Cl$_2$-4-CF$_3$-C$_6$H$_2$ |
| H | C$_2$H$_5$ | CH$_3$ | 0 | 2,6-Cl$_2$-4-CF$_3$-C$_6$H$_2$ |
| H | C$_2$H$_5$ | CH$_3$ | 1 | 2,6-Cl$_2$-4-CF$_3$-C$_6$H$_2$ |
| H | C$_2$H$_5$ | CH$_3$ | 2 | 2,6-Cl$_2$-4-CF$_3$-C$_6$H$_2$ |

-continued $$\begin{array}{c} R^1 \quad\quad S(O)_n-R^2 \\ \diagup \quad \diagdown \\ N \quad\quad\quad R^3 \\ \| \quad\quad / \\ N-N \\ | \\ Ar \end{array} \quad (I)$$

| R¹ | R² | R³ | n | Ar |
|---|---|---|---|---|
| CH₃ | C₂H₅ | CH₃ | 0 | 2,6-Cl₂-4-CF₃-C₆H₂ |
| CH₃ | C₂H₅ | CH₃ | 1 | 2,6-Cl₂-4-CF₃-C₆H₂ |
| CH₃ | C₂H₅ | CH₃ | 2 | 2,6-Cl₂-4-CF₃-C₆H₂ |
| H | i-C₃H₇ | CH₃ | 0 | 2,6-Cl₂-4-CF₃-C₆H₂ |
| H | i-C₃H₇ | CH₃ | 1 | 2,6-Cl₂-4-CF₃-C₆H₂ |
| H | i-C₃H₇ | CH₃ | 2 | 2,6-Cl₂-4-CF₃-C₆H₂ |
| CH₃ | i-C₃H₇ | CH₃ | 0 | 2,6-Cl₂-4-CF₃-C₆H₂ |
| CH₃ | i-C₃H₇ | CH₃ | 1 | 2,6-Cl₂-4-CF₃-C₆H₂ |
| CH₃ | i-C₃H₇ | CH₃ | 2 | 2,6-Cl₂-4-CF₃-C₆H₂ |
| H | CF₃ | CH₃ | 0 | 2,6-Cl₂-4-OCF₃-C₆H₂ |
| H | CF₃ | CH₃ | 1 | 2,6-Cl₂-4-OCF₃-C₆H₂ |
| H | CF₃ | CH₃ | 2 | 2,6-Cl₂-4-OCF₃-C₆H₂ |
| H | CF₂Cl | CH₃ | 0 | 2,6-Cl₂-4-OCF₃-C₆H₂ |
| H | CF₂Cl | CH₃ | 1 | 2,6-Cl₂-4-OCF₃-C₆H₂ |
| H | CF₂Cl | CH₃ | 2 | 2,6-Cl₂-4-OCF₃-C₆H₂ |
| H | CFCl₂ | CH₃ | 0 | 2,6-Cl₂-4-OCF₃-C₆H₂ |

-continued

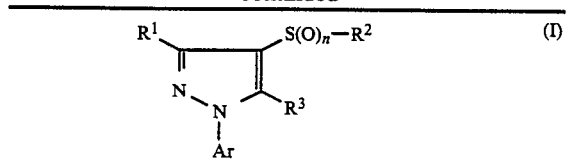

| R¹ | R² | R³ | n | Ar |
|---|---|---|---|---|
| H | CFCl$_2$ | CH$_3$ | 1 | 2,6-dichloro-4-OCF$_3$-phenyl |
| H | CFCl$_2$ | CH$_3$ | 2 | 2,6-dichloro-4-OCF$_3$-phenyl |
| CF$_3$ | CF$_3$ | CF$_3$ | 0 | 2,6-dichloro-4-OCF$_3$-phenyl |
| H | CF$_3$ | CF$_3$ | 0 | 2,6-dichloro-4-OCF$_3$-phenyl |
| H | CH$_3$ | CF$_3$ | 0 | 2,6-dichloro-4-OCF$_3$-phenyl |
| CF$_3$ | CF$_3$ | CF$_3$ | 0 | 2,6-dichloro-4-CF$_3$-phenyl |
| H | CF$_3$ | CF$_3$ | 0 | 2,6-dichloro-4-CF$_3$-phenyl |
| CH$_3$ | CF$_3$ | CF$_3$ | 0 | 2,6-dichloro-4-CF$_3$-phenyl |

-continued

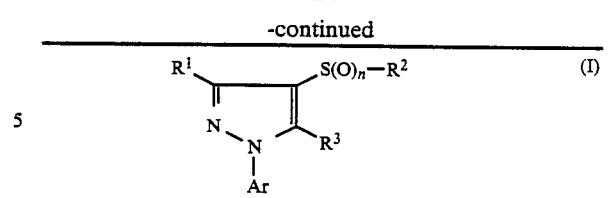

| R¹ | R² | R³ | n | Ar |
|---|---|---|---|---|
| H | CH$_3$ | CF$_3$ | 0 | 2,6-dichloro-4-CF$_3$-phenyl |

If, for example, 2,6-dichloro-4-trifluoromethyl-phenylhydrazine hydrochloride and 1-dimethylamino-2-trifluoromethylthio-but-1-en-3-one are used as starting substances, then the course of the reaction of the process (a) according to the invention can be represented by the following equation:

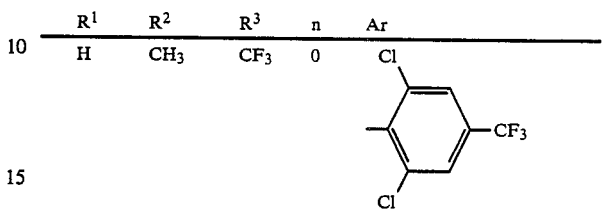

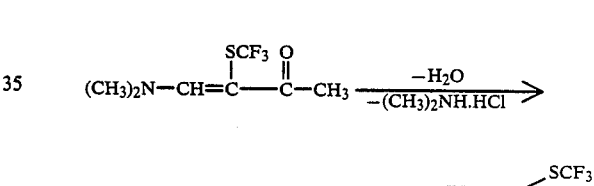

If, for example, 5-amino-1-(2,6-dichloro-4-trifluoromethyl-phenyl)-3-methyl-4-trifluoromethylthio-pyrazole, t-butyl nitrite and benzene are used as starting substances, then the course of the reaction of the process (b) according to the invention can be represented by the following equation:

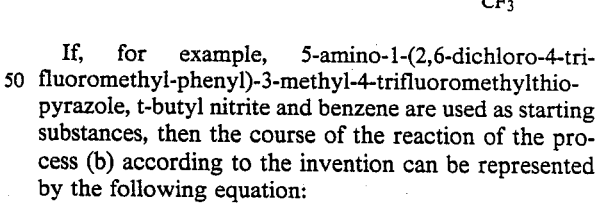

-continued

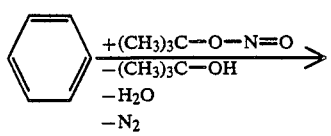

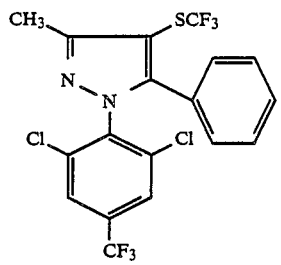

If, for example, 1-(2,6-dichloro-4-trifluoromethyl-phenyl)-5-methyl-4-trifluoromethylthio-pyrazole is used as starting compound and m-chloroperbenzoic acid is used as oxidant, then the course of the reaction of the process (c) according to the invention can be represented by the following equation:

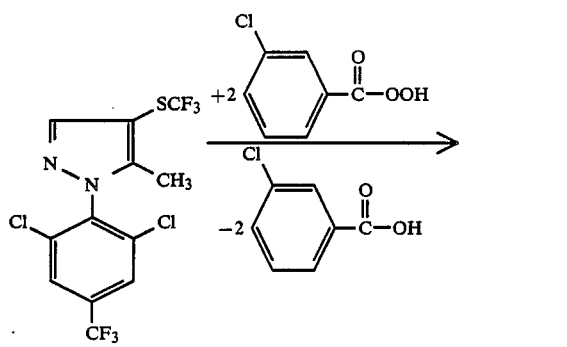

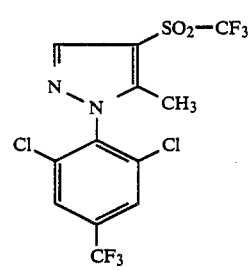

The arylhydrazines which are required as starting substances for carrying out the process (a) according to the invention are generally defined by the formula (II). In this formula (II), Ar preferably represents those radicals which have already been mentioned in connection with the description of the substances, according to the invention, of the formula (I) as being preferred for these substituents.

The arylhydrazines of the formula (II) are known (cf., for example, U.S. Pat. No. 4,127,575; U.S. Pat. No. 3,609,158; DE-OS (German Published Specification) No. 2,558,399; DE-OS (German Published Specification) No. 3,402,308; DE-OS (German Published Specification) No. 3,408,727; J. Chem. Soc. C, 1971, 167-174) or they can be prepared in a simple analogous fashion by processes which are known in principle (cf. Houben-Weyl "Methoden der organischen Chemie [Methods of Organic Chemistry]" Volume X, 2 p. 203, Thieme Verlag Stuttgart 1967), for example by reacting the generally known anilines or pyridylamines of the formula (VII), $$Ar-NH_2 \qquad (VII)$$

in which

Ar has the abovementioned meaning,
with sodium nitrite in the presence of an acid, such as, for example sulphuric acid, and then reacting with tin-II chloride, also in the presence of an acid, such as, for example, hydrochloric acid, at temperatures between $-20°$ C. and $+80°$ C., or by reacting the likewise generally known haloaromatics of the formula (VIII), $$Ar-Hal^1 \qquad (VIII)$$

in which

Ar has the abovementioned meaning and
$Hal^1$ represents halogen, particularly fluorine, chlorine or bromine,
with hydrazine hydrate, if appropriate in the presence of a diluent, such as, for example, pyridine or dioxane, at temperatures between $0°$ C. and $+150°$ C.

The 1,3-diketones which are furthermore required as starting substances for carrying out the process (a) according to the invention are generally defined by the formula (IIIa). In this formula (IIIa), $R^1$, $R^2$ and $R^3$ preferably represent those radicals which have already been mentioned in connection with the description of the substances, according to the invention, of the formula (I) as being preferred for these substituents.

The 1,3-diketones of the formula (IIIa) are known (cf., for example, Chem. Ber. 106, 1418-1422 [1973]; J. org. Chem. 38, 2809-2813 [1973]; J. org. Chem. 46, 153-157 [1981]; J. org. Chem. 49, 3494-3498 [1984]; DE-OS (German Published Specification) No. 2,138,728), or they can be prepared analogously to known processes, for example when 1,3-diketeones of the formula (IX),

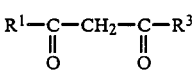

in which $R^1$ and $R^3$ have the abovementioned meaning,
are reacted with sulphenyl chlorides of the formula (X), $$R^2-S-Cl \qquad (X)$$

in which $R^2$ has the abovementioned meaning,
if appropriate in the presence of a diluent, such as, for example, toluene or dioxane, and if appropriate in the presence of an acid acceptor, such as, for example, triethylamine, at temperatures between $0°$ C. and $50°$ C.; or when 2-halo-1,3-diketones of the formula (XI)

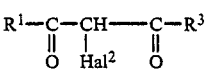

in which $R^1$ and $R^3$ have the abovementioned meaning and
$Hal^2$ represents halogen, particularly chlorine or bromine, are reacted with thiols of the formula (XII), $$R^2\text{—SH} \tag{XII}$$

in which
R² has the abovementioned meaning,
if appropriate in the presence of a diluent, such as, for example, methanol or dimethylformamide, and if appropriate in the presence of an acid acceptor, such as, for example, sodium hydroxide or sodium methylate, at temperatures between 0° C. and 80° C.

The 1,3-diketones of the formula (IX), the sulphenyl chlorides of the formula (X), the 2-halo-1,3-diketones of the formula (XI) and the thiols of the formula (XII) are generally known compounds of organic chemistry.

The α,β-unsaturated ketones which are alternatively required as starting substances for carrying out process (a) according to the invention are generally defined by the formula (IIIb). In this formula (IIIb), R¹, R² and R³ preferably represent those radicals which have already been mentioned in connection with the description of the substances, according to the invention, of the formula (I) as being preferred for these substituents.

A¹ preferably represents methoxy, ethoxy or dimethylamino.

The majority of the α,β-unsaturated ketones of the formula (IIIb) are known (cf., for example, J. org. Chem. 49, 3494–3498 [1984]; Tetrahedron Letters, 3439–3442, 1967, DE-OS (German Published Specification) No. 3,012,597), or they can be prepared analogously to known processes, for example when ketones of the formula (XIII),

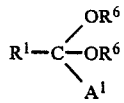

in which
R² and R³ have the abovementioned meaning,
are reacted with orthoesters or amidacetals of the formula (XIV),

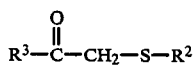

in which
R¹ and A¹ have the abovementioned meaning and
R⁶ represents alkyl, particularly methyl or ethyl,
if appropriate in the presence of a diluent, such as, for example, toluene, and if appropriate in the presence of an acidic catalyst, such as, for example, boron trifluoride etherate, at temperatures between 50° C. and 150° C.

The ketones of the formula (XIII) are known (cf., for example, Chem. Ber. 106, 1418–1422 (1973); DE-OS (German Published Specification) No. 2,138,728; Zh. org. Khim. 8, 1990–1991 (1972); U.S. Pat. No. 3,932,508, U.S. Pat. No. 3,937,738).

The orthoesters or amid acetals of the formula (XIV) are generally known compounds of organic chemistry.

The 5-amino-1-aryl-pyrazoles which are required as starting substances for carrying out the process (b) according to the invention are generally defined by the formula (IV). In this formula (IV), R¹, R² and Ar preferably represent those radicals which have already been mentioned in connection with the description of the substances, according to the invention, of the formula (I) as being preferred for these substituents.

The 5-amino-1-aryl-pyrazoles of the formula (IV) are not yet known. However, they are subject of German Patent Application P No. 3,402,308 and German Patent Application P No. 3,517,843, corresponding respectively to U.S. patent applications Ser. No. 690,347, filed Jan. 10, 1985, now U.S. Pat. No. 4,614,533, and Ser. No. 858,475, filed Apr. 30, 1986, now pending.

They are obtained when 4-thiocyanato-5-amino-pyrazoles of the general formula (XV)

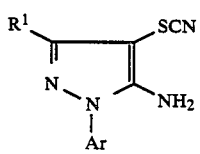

in which
R¹ and Ar have the abovementioned meaning, or bis-(pyrazolyl) disulphides of the formula (XVI)

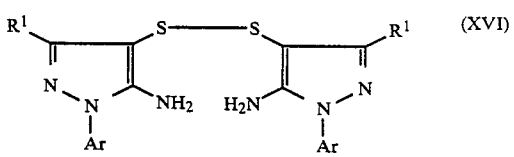

in which
R¹ and Ar have the abovementioned meaning,
are reacted with halides of the formula (XVII), $$R^2\text{—Hal}^3 \tag{XVII}$$

in which
R² has the abovementioned meaning and
Hal³ represents halogen, particularly chlorine, bromine or iodine,
if appropriate in the presence of a diluent, such as, for example, methanol or ethanol, and also if appropriate in the presence of a reducing agent, such as, for example, sodium borohydride or sodium dithionite, and if appropriate in the presence of a base, such as, for example, sodium hydroxide or potassium carbonate, at temperatures between 20° C. and 90° C., or when 4-unsubstituted 5-amino-pyrazoles of the formula (XVIII),

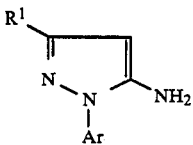

in which
R¹ and Ar have the abovementioned meaning,
are reacted with sulphenyl halides of the formula (XIX), $$R^2\text{—S—Hal}^4 \tag{XIX}$$

in which
R² has the abovementioned meaning and
Hal⁴ represents halogen, particularly fluorine, chlorine, bromine or iodine,
if appropriate in the presence of a diluent, such as, for example, dichloromethane, and if appropriate in the presence of an acid acceptor, such as, for example, pyridine, at temperatures between 0° C. and 50° C.

Some of the 4-thiocyanato-5-aminopyrazoles of the formula (XV) are known (cf., for example, Farmaco Ed. Sci. 38, 274–282 [1983]. They are obtained, for example, when 4-unsubstituted 5-aminopyrazoles of the formula (XVIII),

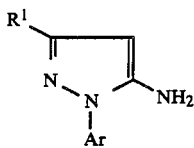
(XVIII)

in which $R^1$ and Ar have the abovementioned meaning, are reacted with ammonium thiocyanate in the presence of bromine and acetic acid at temperatures between −20° C. and +20° C.

The bis-(pyrazole) disulphides of the formula (XVI) are not yet known. They are obtained when the 4-thiocyanato-5-amino-pyrazoles of the formula (XV), described above, are reacted with aqueous hydrochloric acid, if appropriate in the presence of a diluent, such as, for example, ethanol, at temperatures between 20° C. and 120° C.

The halides of the formula (XVII) are generally known compounds of organic chemistry.

Some of the 4-unsubstituted 5-aminopyrazoles of the formula (XVIII) are known (cf., for example, J. Org. Chem. 36, 2972–2974 [1971] or J. Heterocyclic Chemistry 7, 345–349 [1970]; C.A. 62: 13137c).

They are obtained, for example, when arylhydrazines of the formula (II),

(II)

in which

Ar has the abovementioned meaning, are reacted with acrylonitrile derivatives of the formula (XX),

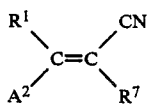
(XX)

in which $R^1$ has the abovementioned meaning, $R^7$ represents hydrogen or alkoxycarbonyl and $A^2$ represents halogen, hydroxyl, alkoxy, amino or dialkylamino, either initially in 1st stage, if appropriate in the presence of a diluent, such as, for example, ethanol or glacial acetic acid, and if appropriate in the presence of a reaction auxiliary such as, for example, sodium acetate, at temperatures between −20° C. and +20° C. to form the arylhydrazine derivatives of the formula (XXI),

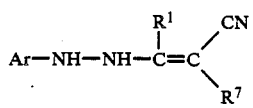
(XXI)

in which

Ar, $R^1$ and $R^7$ have the abovementioned meaning, and cyclizing this in a 2nd stage, if appropriate in the presence of a diluent, such as, for example, ethylene glycol monoethyl ether, at temperatures between +50° C. and +150° C., or cyclizing directly in one reaction step, without isolation of the intermediates of the formula (XXI), if appropriate in the presence of a diluent, such as, for example, ethylene glycol monoethyl ether, at temperatures between +50° C. and +150° C. to form the 5-aminopyrazoles of the formula (XXII),

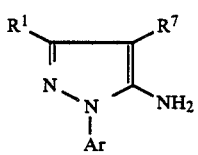
(XXII)

in which $R^1$, $R^7$ and Ar have the abovementioned meaning, and, in the case where $R^7$ represents alkoxycarbonyl, saponifying and decarboxylating the compounds of the formula (XXII), in a generally conventional fashion, if appropriate in the presence of a diluent, such as, for example, ethanol or isopropanol, and if appropriate in the presence of a catalyst, such as, for example, hydrobromic acid, at temperatures between 50° C. and 150° C.

The acrylonitrile derivatives of the formula (XX) are generally known compounds of organic chemistry.

The sulphenyl halides of the formula (XIX) are generally known compounds of organic chemistry.

The aromatics which are furthermore required as starting substances for carrying out the process (b) according to the invention are generally defined by the formula (V). In this formula (V), $R^{3-1}$ preferably represents mono- or polysubstituted phenyl, the substituents being identical or different and suitable substituents being: halogen, cyano, nitro, in each case straight-chain or branched alkyl, alkoxy, alkylthio, alkylsulphinyl, alkylsulphonyl, haloalkyl, haloalkoxy, haloalkylthio, haloalkylsulphinyl or haloalkylsulphonyl having 1 to 4 carbon atoms in each of the individual alkyl moieties and optionally having 1 to 9 identical or different halogen atoms.

$R^{3-1}$ particularly preferably represents mono- to trisubstituted phenyl, the substituents being identical or different and particularly preferred substituents being: fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl or trifluoromethylsulphonyl.

The aromatics of the formula (V) are generally known compounds of organic chemistry.

The alkyl nitrites which are furthermore required as starting substances for carrying out the process (b) according to the invention are generally defined by the formula (VI). In this formula (VI), $R^4$ preferably represents n- or i-propyl, n-, i- or t-butyl, n- or i-hexyl and n- or i-pentyl. $R^4$ particularly preferably represents t-butyl.

The alkyl nitrites of the formula (VI) are also generally known compounds of organic chemistry.

The 1-aryl-pyrazoles which are required as starting substances for carrying out the process (c) according to the invention are generally defined by the formula (Ia). In this formula (Ia), $R^1$, $R^2$, $R^3$ and Ar preferably represent those radicals which have already been mentioned in connection with the description of the substances, according to the invention, of the formula (I) as being preferred for these substituents.

The 1-aryl-pyrazoles of the formula (Ia) are compounds according to the invention and can be obtained with the aid of the processes (a) or (b) according to the invention.

Inert organic solvents are suitable as diluents for carrying out the process (a) according to the invention. These include, in particular, aliphatic or aromatic, optionally halogenated, hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, or alcohols, such as methanol, ethanol or propanol.

If appropriate, the process (a) according to the invention is carried out in the presence of a suitable catalyst. Inorganic mineral acids, such as, for example, hydrochloric acid or sulphuric acid, are particularly suitable as such. It is also possible to employ the arylhydrazines of the formula (II), which are suitable as starting substances, in the form of corresponding acid addition salts, such as, for example, hydrochlorides.

The reaction temperatures can be varied within a relatively wide range when the process (a) according to the invention is carried out. In general, the process is carried out at temperatures between 0° C. and 180° C., preferably at temperatures between 20° C. and 120° C.

To carry out the process (a) according to the invention, 0.5 to 10.0 mols of 1,3-diketone of the formula (IIIa) or of $\alpha,\beta$-unsaturated ketone of the formula (IIIb) and, if appropriate, 0.01 to 1.0 mol of acidic catalyst are generally employed per mol of arylhydrazine of the formula (II) or of a corresponding acid addition salt. The reaction is carried out, and the 1-arylpyrazoles of the formula (Ia) are worked up and isolated by generally conventional methods.

If 1,3-diketones of the formula (IIIa) are used in which the substituent $R^1$ is different to the substituent $R^3$, then isomeric mixtures of compounds of the formula (Ia)

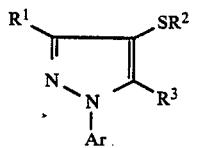

and compounds of the formula (XXIII),

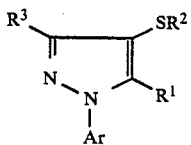

in which $R^1$, $R^2$, $R^3$ and Ar have the abovementioned meaning in both formulae, are obtained as a rule.

The desired reaction products of the formula (Ia) can be isolated from these isomeric mixtures using conventional separation processes (distillation, crystallization, chromatography).

Inert organic solvents are suitable as diluent for carrying out the process (b) according to the invention. These include, in particular, aliphatic, optionally halogenated, hydrocarbons, such as, for example, benzine, petroleum ether, hexane, cyclohexane, dichloromethane, chloroform or carbon tetrachloride.

If the aromatics of the formula (V), which are simultaneously used as reaction components, are present in liquid form at the appropriate reaction temperature, these are used simultaneously as diluents, in appropriate excess, with particular advantage.

The reaction temperatures can be varied within a relatively wide range when the process (b) according to the invention is carried out. In general, the process is carried out at temperatures between $-20°$ C. and $+80°$ C., preferably at temperatures between 0° C. and 50° C.

To carry out the process (b) according to the invention, 1.0 to 3.0 mols, preferably 1.0 to 1.5 mols, of alkyl nitrite of the formula (VI) and 1.0 to 30.0 mols of aromatic of the formula (V) are generally employed per mol of 5-amino-1-aryl-pyrazole of the formula (IV). The reaction is carried out, and the reaction products of the formula (Ib) are worked up and isolated, analogously to known processes.

All oxidants which are conventionally used for sulphur oxidation are suitable as oxidants for carrying out the process (c) according to the invention. Particularly suitable are hydrogen peroxide, organic peracids, such as, for example, peracetic acid, m-chloroperbenzoic acid, p-nitroperbenzoic acid, or atmospheric oxygen.

Inert organic solvents are also suitable as diluent for carrying out the process (c) according to the invention.

Hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethylformamide, are preferably used.

If appropriate, the process (c) according to the invention can be carried out in the presence of an acid acceptor. All organic and inorganic acid acceptors which are conventionally used are suitable as such. Alkaline earth metal or alkali metal hydroxides, acetates or carbonates, such as, for example, calcium hydroxide, sodium hydroxide, sodium acetate or sodium carbonate, are preferably used.

If appropriate, the process (c) according to the invention can be carried out in the presence of a suitable catalyst. All metal salt catalysts which are conventionally customary for such sulphur oxidations are suitable as such. An example which may be mentioned in this connection is ammonium molybdate.

The reaction temperatures can be varied within a relatively wide range when the process (c) according to the invention is carried out. In general, the process is carried out at temperatures between $-20°$ C. and $+70°$ C., preferably at temperatures between 0° C. and $+50°$ C.

To carry out the process (c) according to the invention, 0.8 to 1.2 mols, preferably equimolar amounts, of oxidant are generally employed per mol of 1-arylpyrazole of the formula (Ia) if it is desired to interrupt the oxidation of the sulphur at the sulphoxide state. For oxidation to the sulphone, 1.8 to 3.0 mols, preferably twice the molar amounts, of oxidant are generally employed per mol of 1-aryl-pyrazole of the formula (Ia). The reaction is carried out, and the final products of the formula (Ic) are worked up and isolated by conventional methods.

The active compounds are suitable for combating animal pests, in particular insects and nematodes, encountered in agriculture, in forestry, in the protection of stored products and of materials, and in the hygiene field, and have good plant tolerance and favorable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.*

The active compounds according to the invention are not only active against plant, hygiene and stored product pests, but also, in the veterinary medicine sector, against animal parasites (ectoparasites), such as scaly ticks, argasidae, scab mites, trombidae, flies (stinging and sucking), parasitic fly larvae, lice, hair lice, bird lice and fleas. They are active against normally sensitive and resistant species and strains, as well as against all parasitic and non-parasitic stages of development of the ectoparasites.

The active compounds according to the invention have a strong insecticidal action. They can be employed particularly successfully against insects which are harmful to plants, such as, for example, against the larvae of the mustard beetle (*Phaedon cochleariae*) and against the larvae of the cabbage moth (*Plutella maculipennis*). In addition, they are also extremely suitable for combating soil insects and can be employed, for example, for combating *Phorbia antiqua* grubs or *Diabrotica balteata* larvae in the soil.

In addition, the active compounds according to the invention have a high activity against hygiene pests and stored product pests and can be employed, for example, for combating the house fly (*Musca domestica*), for combating the grain weevil (*Sitophilus granarius*) or for combating German cockroaches (*Blattella germanica*). In addition, the active compounds according to the invention can be particularly successfully used for combating pests which live parasitically on warm-blooded animals, such as, for example, against the larvae of the sheep maggot fly (*Lucilia cuprina*) or against ticks (*Boophilus microplus*).

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, mites, ticks etc. in the sectors of animal keeping and cattle breeding; better results, for example higher milk production, greater weight, more attractive animal pelt, longer life etc., can be achieved by combating the pests.

The application of the active compounds which can be used according to the invention occurs in this sector in a known fashion, such as by oral application in the form of, for example, tablets, capsules, potions, granules, by means of dermal or external application in the form of, for example, dipping, spraying, pouring-on, spotting-on and dusting, as well as by means of parenteral application in the form, for example, of injection, and, furthermore, by means of the feed-through process. In addition, application as moulded articles (collar, ear tag) is also possible.

The biological effectiveness of the compounds according to the invention will be explained with reference to the examples below.

PREPARATION EXAMPLES

Example 1

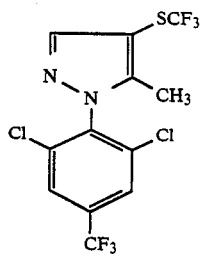

(Process a)

A mixture of 29 g (0.1 mol) of 2,6-dichloro-4-trifluoromethylphenylhydrazine hydrochloride and 21 g (0.1 mol) of 1-dimethylamino-2-trifluoromethylthio-but-1-en-3-one in 150 ml of ethanol is stirred for 16 hours at 70° C. to 75° C. The mixture is worked up by concentrating in vacuo, the residue is taken up in chloroform, washed with water, dried over sodium sulphate and concentrated in vacuo, and the residue is distilled in a high vacuum. 26 g (61% of theory) of 1-(2,6-dichloro-4-trifluoromethyl-phenyl)-5-methyl-4-trifluoromethyl-thiopyrazole of boiling point 140° C. at 0.02 mbar and of melting point 54° C.–56° C. are obtained.

Preparation of the starting compound:

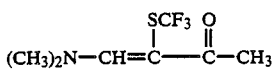

A mixture of 16 g (0.1 mol) of trifluoromethylthioacetone (cf. Chem. Ber. 106, 1418–1422 [1973]) and 20 g (0.16 mol) of N,N-dimethylformamide dimethylacetal is heated for 3 hours at 60° C. The reaction mixture is subsequently distilled. 18 g (84% of theory) of 1-dimethylamino-2-trifluoromethylthio-but-1-en-3-one of boiling point 110° C. at 6 mbar are obtained.

Example 2

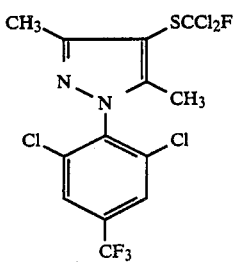

(Process a)

24.5 g (0.1 mol) of 2,6-dichloro-4-trifluoromethylphenylhydrazine and 23.3 g (0.1 mol) of 3-dichlorofluoromethylthio-pentane-2,4-dione in 200 ml of ethanol are refluxed for 24 hours. 4 ml of concentrated sulphuric acid is added to this and the mixture is heated for a further 4 hours at the reflux temperature. The reaction mixture is worked up by concentrating in vacuo, the residue is taken up in dichloromethane, washed with aqueous sodium bicarbonate solution and dried over sodium sulphate, and the solvent is removed in vacuo. 39.2 g (88% of theory) of 1-(2,6-dichloro-4-trifluoromethylphenyl)-3,5-dimethyl-4-dichlorofluoromethylthio-pyrazole are obtained as an oil $^1$H-NMR (CDCl$_3$): $\delta$=7.78 ppm (2H aromatic).

Example 3

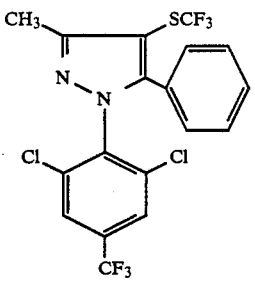

(Process b)

2 ml (0.015 mol) of n-pentyl nitrite are added to 4.1 g (0.01 mol) of 5-amino-1-(2,6-dichloro-4-trifluoromethylphenyl)-3-methyl-4-trifluoromethylthio-pyrazole in 30 ml benzene at room temperature with stirring, and the mixture is stirred for a further 15 hours at room temperature. The mixture is worked up by concentrating in vacuo and the residue is purified by chromatography (silica gel; eluant: petroleum ether/ethyl acetate 9:1). 2.3 g (49% of theory) of 1-(2,6-dichloro-4-trifluoromethylphenyl)-3-methyl-5-phenyl-4-trifluoromethylthio-pyrazole are obtained as an oil.

$^1$H-NMR (CDCl$_3$): $\delta$=7.34 ppm (5H.C$_6$H$_5$).

Preparation of the starting compound:

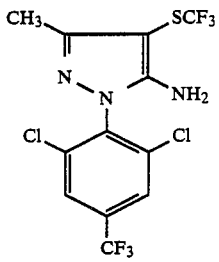

10.2 ml (0.12 mol) of trifluoromethanesulphenyl chloride are added dropwise to 35.4 g (0.114 mol) of 5-amino-1-(2,6-dichloro-4-trifluoromethylphenyl)-3-methylpyrazole and 10 ml (0.125 mol) of anhydrous pyridine in 150 ml of dichloromethane at 0° C. to 5° C. with stirring. After the addition is complete, the mixture is stirred for a further 30 minutes at room temperature 100 ml of dichloromethane are added and the mixture is washed successively with dilute hydrochloric acid, water, sodium bicarbonate solution and aqueous sodium chloride solution and dried over magnesium sulphate, and the solvent is removed in vacuo. 45.8 g (98% of theory) of 5-amino-1-(2,6-dichloro-4-trifluoromethylphenyl)-4-dichlorofluoromethylsulphenyl-3-methyl-pyrazole of melting point 131° C. are obtained.

61.25 g (0.25 mol) of 2,6-dichloro-4-trifluoromethylphenyl-hydrazine and 21 g (0.25 mol) of diacetonitrile in 500 ml of ethanol are refluxed for 20 hours. 4 ml of concentrated sulphuric acid are added to the cooled reaction mixture, which is then heated for a further 4 hours at 60° C. The mixture is worked up by evaporating in vacuo, the residue is taken up in chloroform and rendered alkaline using 25 percent strength aqueous ammonia solution. The organic phase is separated off and the aqueous phase is extracted with chloroform. The combined organic phases are dried over magnesium sulphate and freed of solvent in vacuo.

62 g (80% of theory) of 5-amino-1-(2,6-dichloro-4-trifluoromethylphenyl)-3-methyl-pyrazole are obtained as a glass-like substance.

$^1$H-NMR (CDCl$_3$/TMS)=2.23; 3.50; 5.49; 7.68 ppm.

Example 4

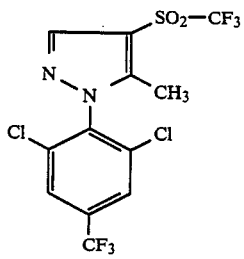

(Process c)

12 g (0.56 mol) of 80 percent strength m-chloroperbenzoic acid are added in portions to 7.9 g (0.02 mol) of 1-(2,6-dichloro-4-trifluoromethylphenyl)-5-methyl-4-trifluoromethylthio-pyrazole in 60 ml of dichloromethane, the mixture is stirred for 40 hours at 25° C. and filtered, the filtrate is washed successively with saturated aqueous sodium bicarbonate solution, saturated aqueous sodium thiosulphate solution and again with saturated aqueous sodium bicarbonate solution, dried over sodium sulphate and concentrated in vacuo. The residue crystallizes on trituration with ligroin. 3.5 g (41% of theory) of 1-(2,6-dichloro-4-trifluoromethylphenyl)-5-methyl-4-trifluoromethylsulphonyl-pyrazole of melting point 83° C.–85° C. are obtained.

The following 1-aryl-pyrazoles of the general formula (I) are obtained in a corresponding fashion and according to the general instructions for the preparation:

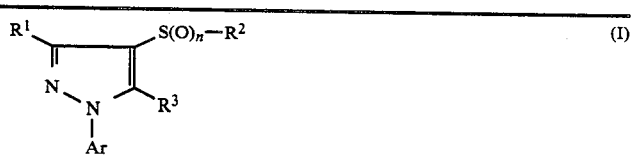

| Ex. No. | $R^1$ | $-S(O)_n-R^2$ | $R^3$ | Ar | Physical Data |
|---|---|---|---|---|---|
| 5 | H | $-S(O)-CF_3$ | $CH_3$ | 2,6-dichloro-4-CF$_3$-phenyl | |
| 6 | H | $-S-CF_2Cl$ | $CH_3$ | 2,6-dichloro-4-CF$_3$-phenyl | B.p. 180° C./0.2 mbar |
| 7 | H | $-S-CF_3$ | 4-i-C$_3$H$_7$-phenyl | 2,6-dichloro-4-CF$_3$-phenyl | $n_D^{20}$ 1.5275 |
| 8 | $CH_3$ | $-S-CCl_2F$ | $CH_3$ | 2-chloro-4-SO$_2$CF$_3$-phenyl | M.p. 69° C.–71° C. |
| 9 | $CH_3$ | $-S-CCl_2F$ | $CH_3$ | 2,6-dichloro-4-SO$_2$CF$_3$-phenyl | M.p. 160° C. |
| 10 | $CH_3$ | $-S-CCl_2F$ | $CH_3$ | 2-chloro-4-OCF$_3$-phenyl | M.p. 49° C.–50° C. |

-continued

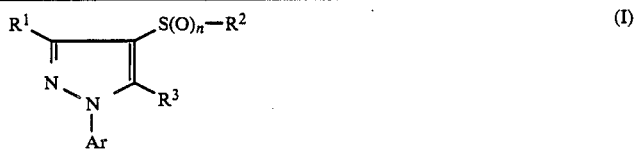
(I)

| Ex. No. | R¹ | —S(O)ₙ—R² | R³ | Ar | Physical Data |
|---|---|---|---|---|---|
| 11 | $CH_3$ | —S—$CF_3$ | 3-methylphenyl (—C₆H₄—$CH_3$) | 2,6-dichloro-4-(trifluoromethyl)phenyl (2,6-Cl₂, 4-$CF_3$) | ¹H—NMR*; 2.51 |
| 12 | $CH_3$ | —S—$CF_2Cl$ | $CH_3$ | 2,6-dichloro-4-(trifluoromethyl)phenyl | ¹H—NMR*; 2.21; 2.43 |
| 13 | $CH_3$ | —S—$CF_3$ | $CH_3$ | 2,6-dichloro-4-(trifluoromethyl)phenyl | ¹H—NMR*; 2.19; 2.40 |
| 14 | H | —S—$CF_3$ | $CH_3$ | 2-chloro-4,6-dibromophenyl | M.p. 55° C.–56° C. |
| 15 | H | —S—$CF_3$ | $CH_3$ | 2,6-dibromo-4-(trifluoromethyl)phenyl | M.p. 80° C.–85° C. |
| 16 | H | —S—$CF_3$ | $CH_3$ | 2,3,6-trichloro-4-(trifluoromethyl)phenyl | M.p. 80° C.–88° C. |
| 17 | $CH_3$ | —S—$CF_3$ | $CH_3$ | 2-chloro-4-(trifluoromethyl)phenyl | ¹H—NMR*; 2.24; 2.39 |
| 18 | $CH_3$ | —S—$CF_3$ | $CH_3$ | 2,6-dichloro-4-(trifluoromethoxy)phenyl | ¹H—NMR*; 2.18; 2.40 |

-continued

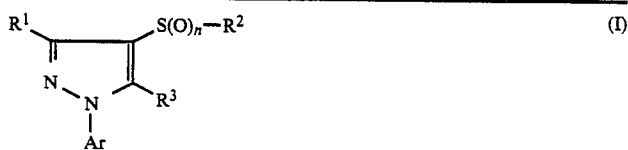

| Ex. No. | R¹ | —S(O)ₙ—R² | R³ | Ar | Physical Data |
|---|---|---|---|---|---|
| 19 | $CH_3$ | —S—$CF_3$ | $CH_3$ | 2,4,6-trichlorophenyl (2,4-Cl, 6-Cl) | ¹H—NMR*; 2.17; 2.38 |
| 20 | H | —S—$CF_3$ | $CH_3$ | 4-bromo-2,6-dichlorophenyl | B.p. 47° C.–49° C. |
| 21 | H | —S—$CF_3$ | i-$C_3H_7$ | 2,6-dichloro-4-(trifluoromethyl)phenyl | B.p. 140° C./0.02 mbar |
| 22 | H | —$SCF_3$ | $CH_3$ | 3-chloro-4-(trifluoromethyl)phenyl | B.p. 180° C./0.2 mbar |
| 23 | H | —$SCF_3$ | $CH_3$ | 4-($SO_2CF_3$)phenyl | M.p. 47° C.–53° C. |
| 24 | H | —$SCF_3$ | $CH_3$ | 2-chloro-6-bromo-4-(trifluoromethyl)phenyl | M.p. 53° C.–56° C. |
| 25 | H | —$SCF_3$ | $CH_3$ | 2,6-dichloro-4-($SCF_3$)phenyl | B.p. 180° C./0.2 mbar |
| 26 | H | —$SCClF_2$ | $CH_3$ | 2-bromo-6-chloro-4-(trifluoromethyl)phenyl | M.p. 59° C.–64° C. |

-continued

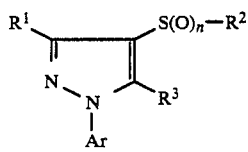

| Ex. No. | R¹ | —S(O)ₙ—R² | R³ | Ar | Physical Data |
|---|---|---|---|---|---|
| 27 | H | —SCClF₂ | CH₃ | 2,6-dichloro-4-SCF₃-phenyl | B.p. 170° C./0.2 mbar |
| 28 | H | —SCClF₂ | CH₃ | 2,6-dibromo-4-CF₃-phenyl | M.p. 79° C.–84° C. |
| 29 | H | —SCClF₂ | CH₃ | 2,6-dichloro-4-Br-phenyl | M.p. 63° C.–65° C. |
| 30 | H | —SCClF₂ | CH₃ | 2,3,6-trichloro-4-CF₃-phenyl | M.p. 64° C.–72° C. |
| 31 | H | —SCClF₂ | CH₃ | 2-chloro-4-CF₃-phenyl | B.p. 170° C./0.2 mbar |
| 32 | CH₃ | —SO—CCl₂F | CH₃ | 2,6-dichloro-4-CF₃-phenyl | |
| 33 | CH₃ | —SO₂CCl₂F | CH₃ | 2,6-dichloro-4-CF₃-phenyl | M.p. 62° C.–65° C. |
| 34 | CH₃ | —S—CClF₂ | CH₃ | 2,6-dichloro-4-OCF₃-phenyl | |

-continued

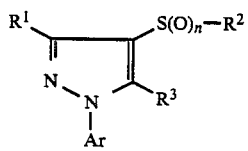

| Ex. No. | R¹ | —S(O)ₙ—R² | R³ | Ar | Physical Data |
|---|---|---|---|---|---|
| 35 | $CH_3$ | —S—$CCl_2F$ | $CH_3$ | 2,6-dichloro-4-($OCF_3$)phenyl | |
| 36 | $CH_3$ | —SO—$CClF_2$ | $CH_3$ | 2,6-dichloro-4-($CF_3$)phenyl | |
| 37 | $CH_3$ | —$SO_2$—$CClF_2$ | $CH_3$ | 2,6-dichloro-4-($CF_3$)phenyl | M.p. 68° C.–70° C. |
| 38 | $CH_3$ | —SO—$CF_3$ | $CH_3$ | 2,6-dichloro-4-($CF_3$)phenyl | M.p. 68° C.–70° C. |
| 39 | $CH_3$ | —$SO_2$—$CF_3$ | $CH_3$ | 2,6-dichloro-4-($CF_3$)phenyl | M.p. 64° C.–66° C. |
| 40 | $CH_3$ | —$SO_2$—$CCl_2F$ | $CH_3$ | 2-chloro-4-($CF_3$)phenyl | M.p. 35° C.–40° C. |
| 41 | $CH_3$ | —$SO_2$—$CCl_2F$ | $CH_3$ | 2-chloro-4-($CF_3$)phenyl | M.p. 88° C.–90° C. |
| 42 | $CH_3$ | —SO—$CClF_2$ | $CH_3$ | 2-chloro-4-($CF_3$)phenyl | |

-continued
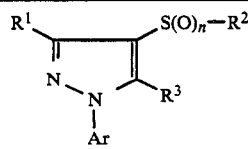
(I)
| Ex. No. | R¹ | —S(O)ₙ—R² | R³ | Ar | Physical Data |
|---|---|---|---|---|---|
| 43 | CH₃ | —SO₂—CClF₂ | CH₃ | 2-Cl, 4-CF₃-phenyl | M.p. 96° C.–97° C. |
| 44 | CH₃ | —SO—CF₃ | CH₃ | 2-Cl, 4-CF₃-phenyl | |
| 45 | CH₃ | —SO₂—CF₃ | CH₃ | 2-Cl, 4-CF₃-phenyl | M.p. 77° C.–78° C. |
| 46 | CH₃ | —S—CF₃ | CH₃ | 2,6-Cl₂, 4-CF₃-phenyl | |
| 47 | H | —SO—CClF₂ | CH₃ | 2,6-Cl₂, 4-CF₃-phenyl | M.p. 79° C.–82° C. |
| 48 | H | —SO₂—CClF₂ | CH₃ | 2,6-Cl₂, 4-CF₃-phenyl | M.p. 70° C.–74° C. |
| 49 | H | —SO₂—CClF₂ | CH₃ | 2,6-Cl₂, 4-Br-phenyl | M.p. 120° C.–121° C. |
| 50 | H | —S—CF₃ | CH₃ | 4-Cl-phenyl | B.p. 180° C./0.7 mbar |
| 51 | H | —S—CF₃ | CH₃ | 2-Cl, 6-F, 3-CF₃, 5-Cl-phenyl | M.p. 78° C.–83° C. |

-continued
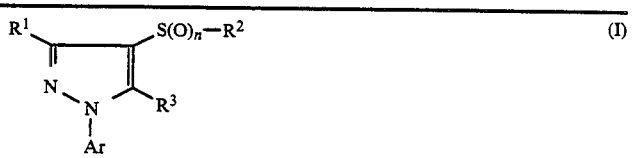
| Ex. No. | R¹ | —S(O)ₙ—R² | R³ | Ar | Physical Data |
|---|---|---|---|---|---|
| 52 | H | —S—CF₃ | CH₃ | 2-Cl, 6-F, 4-CF₃-phenyl | B.p. 160° C./0.4 mbar |
| 53 | H | —S—C₂H₅ | CH₃ | 2,6-diCl, 4-CF₃-phenyl | M.p. 36° C.-38° C. |
| 54 | H | —S—CH(CH₃)₂ | CH₃ | 2,6-diCl, 4-CF₃-phenyl | M.p. 54° C.-56° C. |
| 55 | H | —S—C₆H₅ | CH₃ | 2,6-diCl, 4-CF₃-phenyl | M.p. 85° C.-86° C. |
| 56 | H | —S(O)—CH₃ | CH₃ | 2,6-diCl, 4-CF₃-phenyl | M.p. 114° C. |
| 57 | H | —S(O)—C₂H₅ | CH₃ | 2,6-diCl, 4-CF₃-phenyl | M.p. 89° C. |
| 58 | H | —SO₂—C₂H₅ | CH₃ | 2,6-diCl, 4-CF₃-phenyl | M.p. 102° C.-107° C. |
| 59 | H | —S(O)—CH(CH₃)₂ | CH₃ | 2,6-diCl, 4-CF₃-phenyl | M.p. 70° C. |

-continued

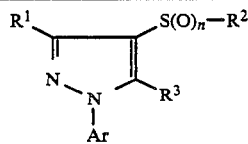

(I)

| Ex. No. | R¹ | —S(O)ₙ—R² | R³ | Ar | Physical Data |
|---|---|---|---|---|---|
| 60 | H | —SO₂—CH(CH₃)₂ | CH₃ | 2,6-Cl₂-4-CF₃-C₆H₂ | M.p. 95° C. |
| 61 | H | —S—CH₂—CH(CH₃)₂ | CH₃ | 2,6-Cl₂-4-CF₃-C₆H₂ | $n_D^{22}$ 1.5325 |
| 62 | H | —S—C₂H₅ | 4-Br-C₆H₄ | 2,6-Cl₂-4-CF₃-C₆H₂ | M.p. 82° C.–84° C. |
| 63 | H | —S—(CH₂)₃—CH₃ | CH₃ | 2,6-Cl₂-4-CF₃-C₆H₂ | $n_D^{21}$ 1.5337 |
| 64 | H | —S—C(CH₃)₃ | CH₃ | 2,6-Cl₂-4-CF₃-C₆H₂ | M.p. 77° C. |

*The ¹H—NMR spectra were recorded in CDCl₃ using tetramethylsilane as internal standard. The chemical shift is given as a δ value in ppm.

Example A

Phaedon larvae test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated smount of emulsifier, and the concentrate is diluted with water to the desired concentration.

Cabbage leaves (Brassica oleacea) are treated by being dipped into the preparation of the active compound of the desired concentration and are infested with mustard beetle larvae (Phaedon cochleariae), as long as the leaves are still moist.

After the specified period of time, the destruction in % is determined. 100% means that all the beetle larvae have been killed.

In this test, the following compounds of the preparation examples, for example, display a superior activity compared to the state of the art: 1, 2, 4, 8, 9, 10, 29, 36, 38, 47 and 53.

Example B

Plutella test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with caterpillars of the diamond-back moth (*Plutella maculipennis*), as long as the leaves are still moist.

After the specified period of time, the destruction in % is determined. 100% means that all the caterpillars have been killed; 0% means that none of the caterpillars have been killed.

In this test, the following compounds of the preparation examples, for example, display superior activity compared to the state of the art: 1, 2, 4, 8 and 10.

Example C

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the following compounds of the preparation examples, for example, display superior activity compared to the state of the art: 1, 2, 4, 6, 11, 12, 17, 18, 19, 20, 24, 35, 37, 38 and 39.

Example D

Test insect: *Diabrotica balteata* larvae in the soil
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparation is of practically no importance here, only the amount by weight of active compound per unit volume of soil, which is given in ppm (mg/l), being decisive. The soil is filled into 0.5 l pots and the pots are left to stand at 20° C.

6 pre-germinated corn kernels are placed in each pot immediately after preparation. After 2 days, the appropriate test insects are introduced into the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the following compounds of the preparation examples, for example, display superior activity compared to the state of the art: 1, 2 and 4.

Example E

Test animals: *Sitophilus granarius*
Number of test animals: 25
Solvent: Acetone 2 parts by weight of active compound are taken up in 1,000 parts by volume of solvent. The solution thus obtained is diluted with further solvent to the desired concentration.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per $m^2$ of filter paper varies, depending on the concentration of the active compound solution. The stated number of test animals is then introduced into the Petri dish, and the dish is covered with a glass lid.

The condition of the test animals is checked 3 days after the experiments have been set up. The destruction in % is determined. 100% means that all the test animals have been killed; 0% means that none of the test animals have been killed.

In this test, the following compounds of the preparation examples, for example, display superior activity compared to the state of the art: 2, 4 and 10.

Example F

Test animals: *Blattella germanica*
Solvent: acetone 2 parts by weight of active compound are taken up in 1,000 parts by volume of solvent. The solution thus obtained is diluted with further solvent to the desired concentration.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per $m^2$ of filter paper varies, depending on the concentration of the active compound solution. The stated number of test animals is then introduced into the Petri dish, and the dish is covered with a glass lid.

The condition of the test animals is checked 3 days after the experiments have been set up. The destruction in % is determined.

In this test, the following compounds of the preparation examples, for example, display superior activity compared to the state of the art: 1 and 2.

Example G

Test animals: *Musca domestica*
Number of test animals: 25
Solvent: Acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filterpaper of about 9.5 cm diameter is located on the bottom of the Petri dish. The Petri dish is left standing open until the solvent has completely evaporated. The amount of active compound per $m^2$ of filterpaper varies, depending on the concentration of the active compound solution. The stated number of test animals is then introduced into the Petri dish, and the dish is covered with a glass lid.

The condition of the test animals is checked continuously. The time required for a 100% knock-down effect is determined.

In this test, the following compounds of the preparation examples, for example, display superior activity compared to the state of the art: 1, 2 and 10.

Example H

Test with *Boophilus microplus* resistant/OP resistant Biarra strain

Solvent:
  35 parts by weight of ethylene glycol monomethyl ether
  35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the desired concentration.

10 adult *Boophilus microplus* res. are immersed for 1 minute in the active compound preparation to be tested. After transfer to plastic beakers and storage in a climatically controlled chamber, the degree of destruction is determined.

In this test, compound 2 of the preparation examples, for example, displays superior activity compared to the state of the art.

Example I

Test with *Lucilia cuprina* res. larvae (OP-res. Goondiwindi strain)

Solvent:
  35 parts by weight of ethylene glycol monomethyl ether
  35 parts of weight of nonylphenol polyglycol ether To produce a suitable preparation of active compound, three parts by weight of active compound are mixed with seven parts by weight of the abovementioned solvent mixture and the concentrate thus obtained is diluted with water to the particular desired concentration.

About 20 *Lucilia cuprina* res. larvae are introduced into a test tube which contains approx. 1 cm³ of horse muscle and 0.5 ml of the preparation of active compound. After 24 hours, the degree of destruction is determined.

In this test, compound 1 of the preparation examples, for example, displays superior activity compared to the state of the art.

It is understood that the specification and examples are illustrative but not limitative of the present invention and that other embodiments within the spirit and scope of the invention will suggest themselves to those skilled in the art.

We claim:

1. A 1-aryl-pyrazole of the formula

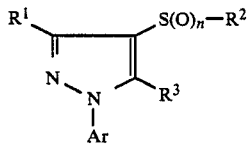

in which
  $R^1$ represents hydrogen, or in each case straight-chain or branched alkyl or haloalkyl having 1 to 4 carbon atoms and optionally 1 to 9 identical or different halogen atoms,
  $R^2$ represents in each case straight-chain or branched alkyl, alkenyl, or alkinyl having up to 8 carbon atoms in each case, cycloalkyl having 3 to 7 carbon atoms, in each case straight-chain or branched haloalkyl or haloalkenyl having up to 8 carbon atoms in each case and up to 17 identical or different halogen atoms, in each case straight-chain or branched alkoxyalkyl, alkylthioalkyl, alkylsulphinylalkyl or alkylsulphonylalkyl having 1 to 6 carbon atoms in each of the individual alkyl moieties, or phenylalkyl or phenyl, optionally having 1 to 4 carbon atoms in the straight-chain or branched alkyl moiety, which is in each case optionally mono- or polysubstituted in the phenyl moiety, the substituents on the phenyl being independently selected from the group consisting of halogen, cyano, nitro, in each case straight-chain or branched alkyl, alkoxy, alkylthio, alkylsulphinyl, alkylsulphonyl, haloalkyl, haloalkoxy, haloalkylthio, haloalkylsulphinyl or haloalkylsulphonyl having 1 to 4 carbon atoms in each of the individual alkyl moieties and optionally having 1 to 9 identical or different halogen atoms,
  $R^3$ represents in each case straight-chain or branched alkyl or haloalkyl having 1 to 6 carbon atoms in each case and optionally having 1 to 12 identical or different halogen atoms or cycloalkyl having 3 to 7 carbon atoms,
  Ar represents mono- or polysubstituted phenyl, with the exception of the 4-nitrophenyl or the 2,4-dinitrophenyl radical, optionally mono- or polysubstituted 2-pyridyl, 3-pyridyl or 4-pyridyl, the substituents being identical or different and in each case being cyano, nitro, halogen, and in each case straight-chain or branched alkyl, alkoxy or alkoxycarbonyl having 1 to 4 carbon atoms in each case, and in addition in each case straight-chain or branched haloalkyl or haloalkoxy having 1 to 4 carbon atoms in each case and 1 to 9 identical or different halogen atoms, or a $—S(O)_p—R^5$ radical,
where
  $R^5$ represents amino and also in each case straight-chain or branched alkyl, alkylamino, dialkylamino or haloalkyl having 1 to 4 carbon atoms in each of the individual alkyl moieties and, in the case of haloalkyl, having 1 to 9 identical or different halogen atoms, and n and p each independently represents a number 0, 1 or 2.

2. A 1-aryl-pyrazole according to claim 1, in which
  $R^1$ represents hydrogen, methyl, ethyl, n- or i-propyl or trifluoromethyl,
  $R^2$ represents methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, cyclopropyl, cyclobutyl, cyclopentyl, cyclohexyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl, fluorochlorobromomethyl, chloroallyl fluoroallyl, chlorobutenyl, fluorobutenyl, dichloroallyl, fluorochloroallyl, difluoroallyl, bromoallyl, methoxymethyl, methoxyethyl, methoxypropyl, ethoxymethyl, ethoxyethyl, methylthiomethyl, methylsulphinylmethyl, methylsulphonylethyl, methylthioethyl, methylthiopropyl, methylsulphinylethyl, methylsulphonylmethyl or in each case optionally mono- to trisubstituted phenyl, benzyl or phenylethyl, the phenyl substituents being independently selected from the group consisting of fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl or trifluoromethylsulphonyl, $R^3$ represents methyl, ethyl, n- or i-propyl, n-, i-, s- or t-butyl, cyclopropyl, cyclobutyl, cyclopentyl, cyclohexyl, chloromethyl, dichloromethyl, trichloromethyl, bromomethyl, dibromomethyl, fluoromethyl, difluoromethyl, trifluoromethyl, fluorodichloromethyl or difluorochloromethyl, Ar represents mono- to pentasubstituted phenyl, with the exception of the 4-nitrophenyl radical or the 2,4-dinitrophenyl radical, the substituents being identical or different, or in each case optionally mono- to tetrasubstituted 2-pyridyl or 4-pyridyl, the substituents being independently selected from the group consisting of cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a —$S(O)_p$—$R^5$ radical, where $R^5$ represents amino, methylamino, ethylamino, dimethylamino, diethylamino, fluorodichloromethyl, difluorochloromethyl, tetrafluoroethyl, trifluorochloroethyl, trifluoromethyl, methyl or ethyl, and p represents a number 0, 1 or 2.

3. A compound according to claim 1, wherein such compound is 1-(2,6-dichloro-4-trifluoromethyl-phenyl)-5-methyl-4-trifluoromethylthio-pyrazole of the formula

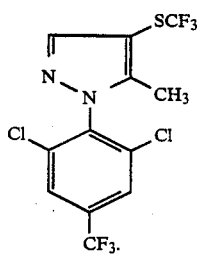

4. A compound according to claim 1, wherein such compound is 1-(2,6-dichloro-4-trifluoromethyl-phenyl)-3,5-dimethyl-4-dichlorofluoromethylthio-pyrazole of the formula

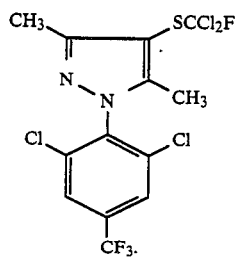

5. A compound according to claim 1, wherein such compound is 1-(2,6-dichloro-4-trifluoromethyl-phenyl)-3,5-dimethyl-4-chlorodifluoromethylthio-pyrazole of the formula

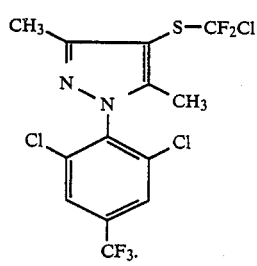

6. A compound according to claim 1, wherein such compound is 1-(4-bromo-2,6-dichlorophenyl)-5-methyl-4-chlorodifluoromethylthio-pyrazole of the formula

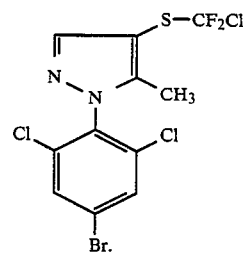

7. A compound according to claim 1, wherein such compound is 1-(2,6-dichloro-4-trifluoromethyl-phenyl)-3,5-dimethyl-4-chlorodifluoromethylsulphinyl-pyrazole of the formula

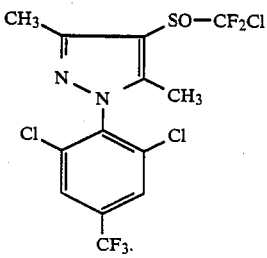

8. A compound according to claim 1, wherein such compound is 1-(2,6-dichloro-4-trifluoromethyl-phenyl)-3,5-dimethyl-4-chlorodifluoromethylsulphonyl-pyrazole of the formula

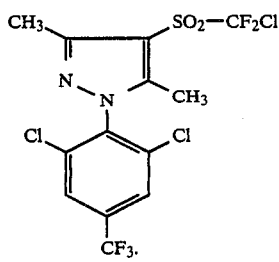

9. A compound according to claim 1, wherein such compound is 1-(2,6-dichloro-4-trifluoromethyl-phenyl)-3,5-dimethyl-4-trifluoromethylsulphinyl-pyrazole of the formula

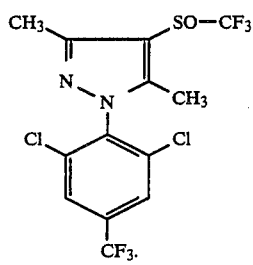

10. A compound according to claim 1, wherein such compound is 1-(2,6-dichloro-4-trifluoromethyl-phenyl)-3,5-dimethyl-4-trifluoromethylsulphonyl-pyrazole of the formula

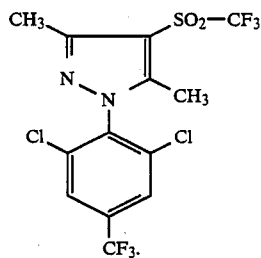

11. A compound according to claim 1, wherein such compound is 1-(2-chloro-4-trifluoromethyl-phenyl)-3,5-dimethyl-4-trifluoromethylsulphonyl-pyrazole of the formula

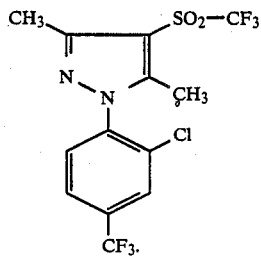

12. A compound according to claim 1, wherein such compound is 1-(2,6-dichloro-4-trifluoromethyl-phenyl)-5-methyl-4-chlorodifluoromethylsulphinyl-pyrazole of the formula

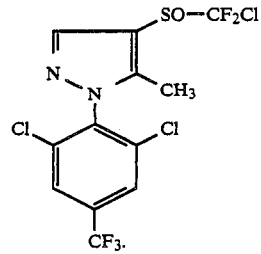

13. A compound according to claim 1, wherein such compound is 1-(2-chloro-6-fluoro-4-trifluoromethyl-phenyl)-5-methyl-4-trifluoromethylthio-pyrazole of the formula

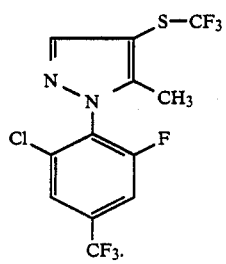

14. The compound according to claim 1, wherein such compound is 1-(2,6-dichloro-4-trifluoromethyl-phenyl)-5-methyl-4-ethylthiopyrazole of the formula

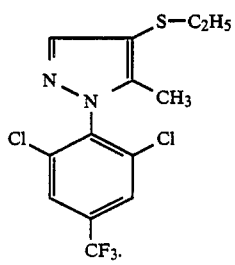

15. A compound according to claim 1, in which $R^3$ represents in each case straight-chain or branched alkyl or haloalkyl having 1 to 6 carbon atoms in each case and optionally having 1 to 12 identical or different halogen atoms.

16. A compound according to claim 1, in which $R^2$ represents in each case straight-chain or branched haloalkyl having up to 8 carbon atoms and in each case up to 17 identical or different halogen atoms.

17. A compound according to claim 1, in which $R^1$ represents hydrogen.

18. An insecticidal composition comprising an insecticidally effective amount of a compound according to claim 1 and a diluent.

19. A method of combating insects which comprises applying to such insects or to an insect habitat an insecticidally effective amount of a compound according to claim 1.

20. The method according to claim 19, wherein such compound is
1-(2,6-dichloro-4-trifluoromethyl-phenyl)-5-methyl-4-trifluoromethylthio-pyrazole,
1-(2,6-dichloro-4-trifluoromethyl-phenyl)-3,6-dimethyl-4-dichlorofluoromethylthio-pyrazole, 1-(2,6-dichloro-4-trifluoromethyl-phenyl)-3,5-dimethyl-4-chlorodifluoromethylthio-pyrazole,
1-(4-bromo-2,6-dichlorophenyl)-5-methyl-4-chlorodifluoromethylthio-pyrazole,
1-(2,6-dichloro-4-trifluoromethyl-phenyl)-3,5-dimethyl-4-chlorodifluoromethylsulphinyl-pyrazole,
1-(2,6-dichloro-4-trifluoromethyl-phenyl)-3,5-dimethyl-trifluoromethylsulphinyl-pyrazole
1-(2,6-dichloro-4-trifluoromethyl-phenyl)-3,5-dimethyl-4-trifluoromethylsulphonyl-pyrazole,
1-(2-chloro-4-trifluoromethyl-phenyl)-3,5-dimethyl-4-trifuoromethylsulphonyl-pyrazole,
1-(2,6-dichloro-4-trifluoromethyl-phenyl)-5-methyl-4-chlorodifluoromethylsulphinyl-pyrazole,
1-(2-chloro-6-fluoro-4-trifluoromethyl-phenyl)-5-methyl-4-trifluoromethylthio-pyrazole or
1-(2,6-dichloro-4-trifluoromethyl-phenyl)-5-methyl-4-ethylthio-pyrazole.

* * * * *

UNITED STATES PATENT AND TRADEMARK OFFICE
CERTIFICATE OF CORRECTION

PATENT NO. : 4,810,720

DATED : March 7, 1989

INVENTOR(S) : Uta Jensen-Korte, et al

It is certified that error appears in the above-identified patent and that said Letters Patent is hereby corrected as shown below:

| | |
|---|---|
| Col. 5, line 6 | Delete "tifluoromethylsulpho-" and substitute --trifluoromethylsulpho- -- |
| Col. 44, line 39 | Before "in" delete "and" |
| Col. 48, line 30 | Delete "The compound" and substitute --A compound-- |
| Col. 48, line 67 | End of line delete "3,6-" and substitute -- 3,5- -- |

Signed and Sealed this

Fourteenth Day of May, 1991

Attest:

Attesting Officer

HARRY F. MANBECK, JR.

Commissioner of Patents and Trademarks